US00PP33640P2

(12) United States Plant Patent
van Sambeek

(10) Patent No.: US PP33,640 P2
(45) Date of Patent: Nov. 16, 2021

(54) LEUCANTHEMUM PLANT NAMED 'DOLEUSWEDARE'

(50) Latin Name: *Leucanthemum maximum*
Varietal Denomination: Doleuswedare

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/139,937

(22) Filed: Dec. 31, 2020

(51) Int. Cl.
*A01H 6/14* (2018.01)
*A01H 5/02* (2018.01)

(52) U.S. Cl.
USPC ..... Plt./285

(58) Field of Classification Search
USPC ..... Plt./285
See application file for complete search history.

(56) References Cited

PUBLICATIONS

PLUTO Plant Variety Database Apr. 23, 2021.*

* cited by examiner

*Primary Examiner* — Annette H Para
(74) *Attorney, Agent, or Firm* — C. Anne Whealy

(57) ABSTRACT

A new and distinct cultivar of *Leucanthemum* plant named 'Doleuswedare', characterized by its upright and mounded plant habit; freely branching habit; strong and upright flowering stems; early and freely flowering habit; large spider-type inflorescences with white-colored ray florets and bright yellow-colored disc florets; good inflorescence longevity; and good garden performance.

1 Drawing Sheet

Botanical designation: *Leucanthemum maximum.*
Cultivar denomination: 'DOLEUSWEDARE'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 24, 2020, application number 2020/1984. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Leucanthemum* plant, botanically known as *Leucanthemum maximum* and hereinafter referred to by the name 'Doleuswedare'.

The new *Leucanthemum* plant is a product of a planned breeding program conducted by the Inventor in Aalsmeer, The Netherlands. The objective of the breeding program is to create new *Leucanthemum* plants with numerous unique and attractive inflorescences.

The new *Leucanthemum* plant originated from a cross-pollination in June, 2014 of a proprietary selection of *Leucanthemum maximum* identified as code number LC-0021, not patented, as the female, or seed, parent with a proprietary selection of *Leucanthemum maximum* identified as code number LC-0026, not patented, as the male, or pollen, parent. The new *Leucanthemum* plant was discovered and selected by the Inventor as a single flowering plant from within the progeny of the stated cross-pollination in a controlled environment in Aalsmeer, The Netherlands in April, 2015.

Asexual reproduction of the new *Leucanthemum* plant by vegetative terminal cuttings in Aalsmeer, The Netherlands, since May, 2015 has shown that the unique features of this new *Leucanthemum* plant are stable and reproduced true to type in successive generations.

SUMMARY OF THE INVENTION

Plants of the new *Leucanthemum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Doleuswedare'. These characteristics in combination distinguish 'Doleuswedare' as a new and distinct *Leucanthemum* plant:

1. Upright and mounded plant habit.
2. Freely branching habit.
3. Strong and upright flowering stems.
4. Early and freely flowering habit.

5. Large spider-type inflorescences with white-colored ray florets and bright yellow-colored disc florets.
6. Good inflorescence longevity.
7. Good garden performance.

Plants of the new *Leucanthemum* differ primarily from plants of the female parent selection in ray floret size as ray florets of plants of the new *Leucanthemum* are broader than ray florets of plants of the female parent selection.

Plants of the new *Leucanthemum* differ primarily from plants of the male parent selection in inflorescence type as plants of the new *Leucanthemum* have spider-type inflorescences whereas plants of the male parent selection have decorative-type inflorescences.

Plants of the new *Leucanthemum* can be compared to plants of *Leucanthemum* x *superbum* 'Goldfinch', disclosed in U.S. Plant Pat. No. 24,499. In side-by-side comparisons, plants of the new *Leucanthemum* differ from plants of 'Goldfinch' in the following characteristics:

1. Plants of the new *Leucanthemum* flower earlier than plants of 'Goldfinch'.
2. Plants of the new *Leucanthemum* have spider-type inflorescences whereas plants of 'Goldfinch' have decorative-type inflorescences.
3. Ray florets of plants of the new *Leucanthemum* are white in color whereas ray florets of plants of 'Goldfinch' are yellow in color.

BRIEF DESCRIPTION OF THE PHOTOGRAPH

The accompanying colored photograph illustrates the overall appearance of the new *Leucanthemum* plant showing the colors as true as it is reasonably possible to obtain in colored reproductions of this type. Colors in the photograph may differ slightly from the color values cited in the detailed botanical description which accurately describe the colors of the new *Leucanthemum* plant. The photograph is a side perspective view of a typical flowering plant of 'Doleuswedare' grown in a container.

DETAILED BOTANICAL DESCRIPTION

The aforementioned photograph and following observations and measurements describe plants grown in 13-cm containers in Aalsmeer, The Netherlands during the early summer initially in a greenhouse and finished in an outdoor nursery and under conditions and cultural practices which approximate those generally used in commercial *Leucanthemum* plant production. During the production of the plants, day temperatures averaged 21° C. and night temperatures averaged 15° C. Plants were 20 weeks old when the photographs and description were taken. In the following description, color references are made to The Royal Horticultural Society Colour Chart, Second Edition, except where general terms of ordinary dictionary significance are used. Measurements represent averages for typical flowering plants.

Botanical classification: *Leucanthemum maximum* 'Doleuswedare'.

Parentage:

*Female, or seed, parent*.—Proprietary selection of *Leucanthemum maximum* identified as code number LC-0021, not patented.

*Male, or pollen, parent*.—Proprietary selection of *Leucanthemum maximum* identified as code number LC-0026, not patented.

Propagation:

*Type*.—Terminal vegetative cuttings.

*Time to initiate roots, summer*.—About twelve days at temperatures about 26° C.

*Time to initiate roots, winter*.—About two weeks at temperatures about 23° C.

*Time to produce a rooted young plant, summer*.—About two weeks at temperatures about 23° C.

*Time to produce a rooted young plant, winter*.—About 16 days at temperatures about 18° C.

*Root description*.—Medium in thickness, fibrous; typically white to light brown in color, actual color of the roots is dependent on substrate composition, water quality, fertilizer type and formulation, substrate temperature and physiological age of roots.

*Rooting habit*.—Moderately freely branching, medium density.

Plant description:

*Plant and growth habit*.—Herbaceous perennial; upright and mounded plant habit; moderately vigorous growth habit; moderate growth rate; freely branching habit with about twelve primary branches developing per plant.

*Plant height*.—About 33 cm.

*Plant width*.—About 39 cm.

*Branch description*.—Length: About 36 cm. Diameter: About 5 mm. Internode length: About 2 cm to 6 cm. Strength: Strong. Aspect: About 20° to 60° from vertical. Texture and luster: Pubescent; semi-glossy. Color: Close to 146A.

*Leaf description*.—Arrangement: Alternate; simple; sessile. Length: About 12 cm. Width: About 2 cm. Shape: Oblong to spatulate. Apex: Acuminate. Base: Cuneate. Margin: Serrate. Texture and luster, upper and lower surfaces: Smooth, glabrous; semi-glossy. Venation pattern: Pinnate. Color: Developing leaves, upper and lower surfaces: Close to 137B. Fully developed leaves, upper surface: Close to 137B; venation, close to 138C. Fully developed leaves, lower surface: Close to 137B; venation, close to 138C.

Inflorescence description:

*Appearance*.—Large inflorescences with oblong-shaped ray florets and tubular disc florets; inflorescences held upright on strong peduncles, inflorescences face mostly upright; ray and disc florets develop acropetally on a capitulum.

*Fragrance*.—Slightly fragrant, pleasant.

*Flowering response*.—Plants begin flowering about eleven weeks after planting; plants flower naturally during June and July in The Netherlands.

*Postproduction longevity*.—Inflorescences maintain good substance for about six to eight weeks on the plant; inflorescences persistent.

*Quantity of inflorescences*.—Freely flowering habit, about 31 inflorescences develop per plant during the flowering season.

*Inflorescence size*.—Diameter: About 7 cm. Depth (height): About 2 cm. Disc diameter: About 2 cm.

*Receptacles*.—Height: About 5 mm. Diameter: About 3 cm. Color: Close to 147B.

*Inflorescence buds*.—Height: About 1 cm. Diameter: About 1.5 cm. Shape: Flattened sphere. Texture and luster: Smooth, glabrous; glossy. Color: Close to 157A.

*Ray florets*.—Quantity per inflorescence: About 55 arranged in about seven whorls. Length: About 3 cm. Width: About 2.5 cm. Shape: Oblong in overall shape, tri-lobed. Apex: Emarginate. Base: Fused at the base. Margin: Entire; moderately undulate. Aspect: Mostly horizontal to reflexing with development. Texture and luster, upper and lower surfaces: Smooth, glabrous; matte. Color: When opening and fully opened, upper surface: Close to 155D; color does not change with development. When opening and fully opened, lower surface: Close to 155D; color does not change with development.

*Disc florets*.—Quantity per inflorescence: About 500 massed at the center of the receptacle arranged in about 14 whorls. Length: About 8 mm. Diameter: About 1 mm. Shape: Fused tubular. Apex: Acute, five-pointed. Texture and luster, inner and outer surfaces: Smooth, glabrous; matte. Color: When opening and fully opened, inner surface: Close to 17A; color does not change with development. When opening and fully opened, outer surface: Close to 17A; proximally, close to 144C; color does not change with development.

*Involucral bracts*.—Quantity per inflorescence: About 50 arranged in about three whorls. Length: About 1 cm. Width: About 3 mm. Shape: Subulate. Apex: Acuminate. Base: Fused. Margin: Entire. Texture and luster, upper and lower surfaces: Smooth, glabrous; semi-glossy. Color, upper and lower surfaces: Close to 147B.

*Peduncles*.—Length: About 14 cm to 27 cm. Diameter: About 4 mm. Strength: Moderately strong. Aspect: About 10° to 20° from vertical. Texture and luster: Slightly pubescent; semi-glossy. Color: Close to 146A.

*Reproductive organs*.—Androecium: Present on disc florets only. Quantity per floret: Five per disc floret. Filament length: About 1 mm. Filament color: Close to 142A. Anther shape: Roughly rectangular. Anther size: About 1 mm by 4 mm. Anther color: Close to 145A. Pollen amount: Abundant. Pollen color: Close to 17A. Gynoecium: Present on ray and disc florets. Quantity per floret: One. Pistil length: About 5 mm. Stigma diameter: Close to 1.5 mm. Stigma shape: Bi-parted. Stigma color: Close to 145A. Style length: About 4 mm. Style color: Close to 145A. Ovary color: Close to 145A.

*Seeds and fruits*.—To date, seed and fruit development have not been observed on plants of the new *Leucanthemum*.

Pathogen & pest resistance: To date, plants of the new *Leucanthemum* have not been observed to be resistant to pathogens and pests common to *Leucanthemum* plants.

Garden performance: Plants of the new *Leucanthemum* have exhibited good tolerance to rain, wind and to tolerate temperatures ranging from −30° C. to about 35° C. and to be suitable for USDA Hardiness Zone 4.

It is claimed:

1. A new and distinct *Leucanthemum* plant named 'Doleuswedare' as illustrated and described.

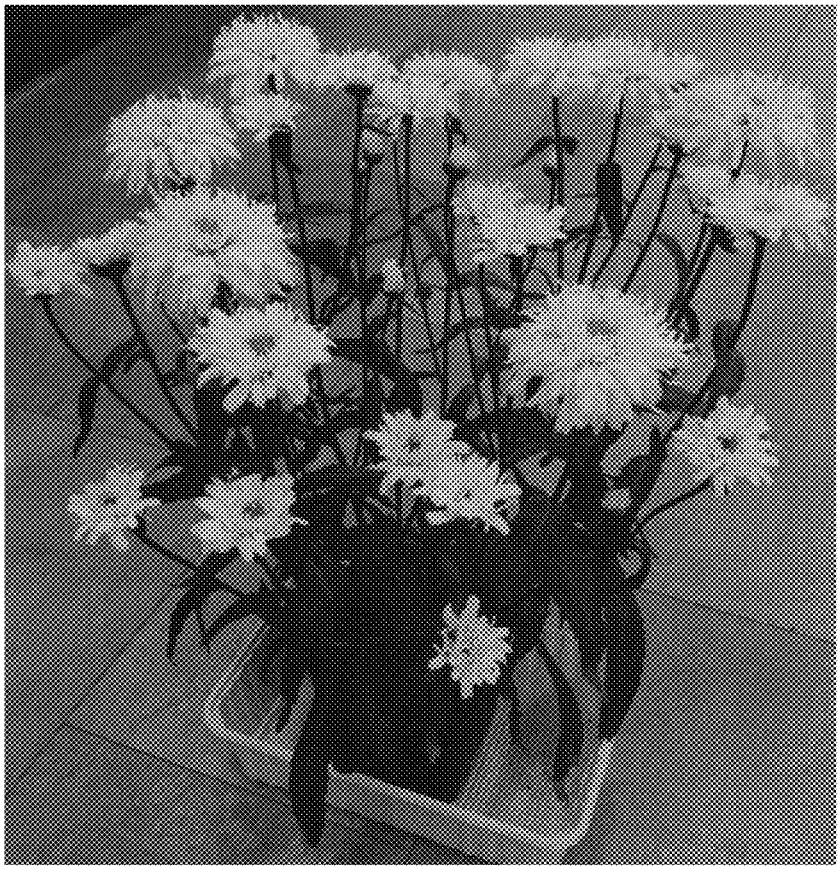

* * * * *